United States Patent [19]

Campbell et al.

[11] 4,075,193
[45] Feb. 21, 1978

[54] PROCESS FOR PRODUCING INTRAVENOUS IMMUNE GLOBULIN

[75] Inventors: Cyrill John Campbell, Detroit; Daniel Ting Hsiu Liu, Sterling Heights, both of Mich.

[73] Assignee: Parke, Davis & Company, Detroit, Mich.

[21] Appl. No.: 744,906

[22] Filed: Nov. 26, 1976

[51] Int. Cl.$^2$ .................... A23J 1/06; A61K 35/14
[52] U.S. Cl. .................... 260/112 B; 424/101
[58] Field of Search .................... 260/112 B; 424/101, 424/177

[56] References Cited

U.S. PATENT DOCUMENTS

| | | | |
|---|---|---|---|
| 3,449,316 | 6/1969 | Querry | 260/112 B |
| 3,808,124 | 4/1974 | Dziobkowski et al. | 260/112 B X |
| 3,943,245 | 3/1976 | Silverstein | 424/101 |
| 3,966,906 | 6/1976 | Schultze et al. | 424/177 X |

OTHER PUBLICATIONS

Deutsch et al., *Science*, vol. 170, pp. 1095–1096 (1970).
Liu et al., *Can. J. Biochem.*, vol. 49, pp. 1056–1061 (1971).

*Primary Examiner*—Walter C. Danison
*Attorney, Agent, or Firm*—David B. Ehrlinger; Stephen Raines; Frank S. Chow

[57] ABSTRACT

A process is provided for producing intravenous immune globulin which comprises adsorbing plasminogen from blood of a selected mammalian species on L-lysine agarose, washing the adsorbate and eluting the purified plasminogen, converting the plasminogen to plasmin, and incubating a mixture of the plasmin and homospecific immune globulin having anticomplementary activity so as to reduce the anticomplementary activity, adsorbing excess plasmin present in the mixture, and recovering the immune globulin from the mixture.

10 Claims, No Drawings

PROCESS FOR PRODUCING INTRAVENOUS IMMUNE GLOBULIN

SUMMARY AND DETAILED DESCRIPTION

This invention relates to a process for producing immune globulin adaptable for intravenous administration, and more particularly, to such a process in which immune globulin, also known as immunoglobulin, having anticomplementary activity is treated with an enzyme to provide a compatible immune globulin for intravenous therapy.

In the past immune globulin, and specifically immune serum globulin, preparations have been used for prophylactic and therapeutic purposes, administered primarily through intramuscular or subcutaneous injections. However, there are limiting factors when utilizing these routes, such as the maximum volume of solution which can be injected in each site. Also, there is a delay from the time of injection to the attainment of maximum antibody levels in the bloodstream. Finally, there is a loss of the antibody during the passage from the injection site to the blood compartment. Therefore, there is a need for an effective means such as intravenous injection of delivering immune serum globulin directly and promptly to the bloodstream. However, in the typical case when immune serum globulin (of the kind presently used for intramuscular injection) is used intravenously, untoward reactions occur in the recipients. The untoward reactions are thought to be caused by the anticomplementary activity associated with the immune serum globulins being used. Consequently, it is though that this activity has to be somehow eliminated or reduced in order to make the immune serum globulin preparations suitable for intravenous use. Known methods for removing anticomplementary activity from immune serum globulin include removal of aggregates by ultracentrifugation and treatment with enzymes or chemicals to obtain modified immune serum globulin. The known methods for removing anticomplementary activity have, however, been impractical.

It is therfore an object of the present invention to provide an improved process for producing immune globulin adaptable for intravenous administration.

In accordance with the invention, there is provided a process for producing immune globulin adaptable for intravenous administration which comprises adsorbing plasminogen derived from blood of a selected mammalian species on an adsorbent substrate of L-lysine agarose, washing the adsorbate to elute impurities, eluting the purified plasminogen from the substrate, converting the eluted plasminogen to plasmin, incubating a mixture of said plasmin and a quantity of homospecific immune globulin having anticomplementary activity under conditions such that the anticomplementary activity is substantially reduced, inactivating plasmin present in said mixture by adsorption on an inactivation adsorbent for plasmin, and recovering the immune globulin from the mixture. The process is subject to wide variation, and in general, the process conditions are not critical. For the first step of adsorbing plasminogen, mammalian blood (that is whole blood, a placental blood, a blood serum or plasma, a serum or plasma fraction, or a Cohn fraction III, or the like) is a suitable source of plasminogen, the mammalian species selected being the same as that from which the intended immune globulin product is derived. In other words, the immune globulin used in the process is homospecific with the species which is the source of the plasminogen used. For example, in producing a human immune globulin product according to the invention, one uses human plasminogen and human immune globulin starting material; for producing a bovine product one uses bovine plasminogen and bovine immune globulin starting material. The adsorption substrate used is L-lysine agarose. The plasminogen is conveniently used in aqueous extract form obtained, for example, as the supernatant from a centrifuged suspension of a suitable plasminogen source such as Cohn III paste in buffered saline. The aqueous plasminogen extract and L-lysine agarose in gel form are mixed in the cold to achieve adsorption of the plasminogen on the gel, the gel is washed with buffered saline and the washed gel is eluted with L-lysine to provide the desired purified plasminogen in solution. A preferred method of washing is described in U.S. Pat. No. 3,943,245. For the subsequent step of converting plasminogen to plasmin, the plasminogen solution can be used directly; in other words, it is unnecessary to isolate or recover the plasminogen from the lysine solution. The L-lysine agarose in at least one of its forms is a known material made, for example, from agarose activated by cyanogen bromide and covalently linked to L-lysine hydrochloride [prepared as described in Science, Vol. 170, pages 1095–1096 (1970) and Can. J. Biochem., Vol. 49, pages 1056–1061 (1971), which description is incorporated herein by reference]. The term, L-lysine agarose, as used herein includes such material made from agarose or cross-linked agarose (such as cross-linked agarose known as Sepharose ® CL-4B, available from Pharmacia Fine Chemicals AB) prepared by reacting agarose with, for example, epihalohydrin or with a compound which under the reaction conditions acts as a source of epihalohydrin such as 2,3-dibromopropanol, under strongly alkaline conditions (British Pat. No. 1,352,613). The use of autoclavable L-lysine cross-linked agarose is preferred, and such use is a feature of the invention, since it has been found unexpectedly that in successive runs L-lysine cross-linked agarose can be used repeatedly as an affinity chromatography substrate (and autoclaved each time for sterility purposes) without losing its binding capacity to plasminogen. Thus, a comparison of plasminogen preparations made by affinity chromatography using either the autoclaved or non-autoclaved L-lysine cross-linked agarose revealed no significant difference between these two preparations with respect to yield or specific activity.

The eluate containing plasminogen is conveniently purified prior to further use. This can be done in any suitable way. A preferred method of purification involves isolating the plasminogen as a precipitate obtained by salting out with ammonium sulfate and centrifugation. The precipitate is taken up in buffered saline, dialyzed against saline, and sterile filtered.

The plasminogen can be converted to its active enzyme plasmin using any of various methods and activators. A preferred procedure is to admix the plasminogen concentrate and sterile glycerol solution and to hold the mixture until activation is complete (usually from 1 to 2 weeks at 35° C.) as determined by assay.

The purified plasmin solution may be used directly for incubation with immune globulin, according to the invention, to reduce anticomplementary activity associated with the globulin. The invention in this respect contemplates the use of any of the various animal and human immune globulins, for example, immune human serum globulin, Rho(D) immune human globulin, pseudomonas immune human globulin, vaccinia immune human globulin, pertussis immune human globulin, and the like. The immune globulin is conveniently used for this purpose as an aqueous solution reconstituted from lyophilized powder obtained from plasma fractionated by the Cohn process. The aqueous immune globulin solution conveniently is in sterile form suitable for parenteral administration, constituted, for example, in one preferred embodiment to contain 16.5% protein, 2.25% glycine, and 0.2% sodium chloride, and adjusted to pH 6.8 with sodium acetate buffer. For incubation, the plasmin solution is admixed with the immune globulin solution and held suitably at ambient temperature for a period to accomplish a continuing enzymatic reduction of the anticomplementary activity associated with the immune globulin solution starting material. The concentration of plasmin used for the purpose should be sufficiently high to reduce the anticomplementary activity within reasonable periods and yet not so high as to cause undue protein fragmentation. For example, using purified human plasmin at a ratio of 0.5 to 1.0 CTA unit (caseinolytic assay unit, Committee on Thrombolytic Agents) to each milliliter of immune globulin solution, the incubation typically may require from 2 to 9 days or longer depending on various empirical factors associated with each lot of globulin solution starting material such as initial anticomplementary activity, susceptibility to protein fragmentation, etc. In order to follow the course of incubation, aliquots of the mixture can be obtained from time to time and assayed for anti-complementary activity and protein distribution.

The anticomplementary activity, expressed as milligrams of protein per milliliter, required to inhibit two units of complement as determined by 50% hemolysis of sensitized sheep red cells (mg./ml./2CH50), is determined by a standard assay procedure reported in U.S. Department of Health, Education and Welfare Public Health Monograph No. 74, Standardized diagnostic complement fixation method and adaptation to micro test.

The protein distribution is conveniently determined by column chromatography. In a preferred procedure using a dextran column (Sephadex ®: G-200, 2.5 × 90 cm., equilibrated with 0.02 M sodium acetate buffer containing 0.15M sodium chloride at pH 7.0), a 1-milliliter aliquot of incubated globulin solution is applied to the columm and the column eluted with the same buffer at a flow rate of 15 ml. per hour. Effluent is collected in 9-milliliter fractions with a fraction collector equipped with automatic recording of ultraviolet absorption at a wave-length of 280 nanometers (nm). From the elution volume, the molecular weight spectrum of the sample can be determined by comparison with a standard curve showing the relationship between the elution volume and the molecular weights of standard proteins, preliminarily established with the same column. For determination of percent protein distribution on the chromatogram, the fractions under a given protein peak are pooled, assayed for protein content by absorption at 280 nm., and the percentage of protein at each peak vis-a-vis total protein is calculated.

During the incubation, when the anticomplementary activity of the immune globulin is sufficiently reduced, preferably when the anticomplementary activity is at a level of at least about 10 mg./ml./2CH5O or higher, and also preferably when the immune globulin is fragmented by not more than about 25%, the residual plasmin remaining in the solution is removed from the solution by adsorbing the plasmin on an inactivation adsorbent for plasmin, conveniently by mixing at room temperature for two to three hours. Although any of various purified inert adsorbent materials, for example, bentonite, charcoal, silica dioxide, kaolin, montmorillonite, etc., are suitable for the purpose, bentonite is a preferred adsorbent. The desired immune globulin solution, free from plasmin in a form suitable for intravenous administration, is recovered by removing the solid adsorbent by centrifugation or other suitable means. In one preferred procedure the adsorbent is removed by centrifugation at 12,000 g. for 20 minutes, the supernatant plasmin-free immune globulin solution is then sterile filtered through a series of membranes of decreasing porosity to a mean pore size of 0.22 to 0.3 microns.

The process of the invention can be used for producing any of various immune globulins adapted or adaptable for intravenous administration, such as immune human serum globulin, pertussis immune human globulin, tetanus immune human globulin, vaccinia pseudomonas immune human globulin, and the like, starting with the respective untreated immune globulin which contains excessive anticomplementary activity and which is therefore unsuitable for intravenous administration. The mentioned sterile supernatant immune globulin solution typically made to contain 16.5% protein (>90% gamma globulin) in 0.3 M glycine, 0.2% NaCl solution at pH $6.8 \pm 0.4$, can be used as it is for intravenous injection. It may, however, be diluted aseptically to any desired protein concentration with sterile physiological saline permitting thereby a proportional decrease in the rate of administration.

The invention is illustrated by the following example.

A. Preparation of Lysine Cross-linked Agarose

1. Pour the contents of a 1-liter bottle of chromatograph cross-linked agarose gel (Sepharose ® CL-4B, Pharmacia AB) into a 4-liter beaker. Rinse the bottle with distilled water and pour into the beaker. Add more distilled water to the beaker until the total volume of the gel suspension reaches 2 liters. (One liter of gel and 1 liter of water.)

2. Scoop with a spatula the contents of a 100-gram bottle of cyanogen bromide and transfer to a 2-liter beaker. Add 1 liter of distilled water to the beaker and mix with a magnetic stirrer until cyanogen bromide is dissolved.

3. Pour the cyanogen bromide solution into the 2-liter gel suspension, mixing with a magnetic stirrer. The pH of the mixture is maintained at 11 by addition of 4 N sodium hydroxide solution. Addition of sodium hydroxide continues until the reaction ends (no further change in pH). It takes about 220 ml. of sodium hydroxide solution to complete the reaction.

4. Pour the gel suspension to a sintered glass funnel and filter with suction. Wash the gel with 10 liters of cold 0.1 M sodium bicarbonate. After wash, suspend the gel in 1 liter of 0.1 M sodium bicarbonate at pH 9.0.

5. Prepare a 20% lysine solution by dissolving 100 grams of L-lysine hydrochloride in 500 ml. of distilled water and titrated to pH 8.9 by adding 4 N sodium hydroxide. This lysine solution should be prepared beforehand and kept at 4° C. When step 4 is completed, add the lysine solution quickly to the cyanogen bromide activated agarose gel and mix at 4° C. for 24 hours.

6. Wash the lysine-agarose gel with 12 liters of distilled water on a sintered glass funnel. Suspend the gel in 1 liter of distilled water. Autoclave the gel suspension at 120° C. for 30 minutes. Store it aseptically at 4° C.

B. Preparation of Human Plasminogen Concentrate

1. Mix 300 grams of Cohn fraction III paste with 1.5 liters of phosphate buffered saline (0.01 M phosphate, 0.14 M NaCl at pH 7.4) overnight at 4° C. Centrifuge the suspension at 12,000xg for 20 minutes. The supernatant is collected and assayed for plasminogen activity using the Hammarsten casein assay described below.

2. Mix 1 liter of the autoclaved lysine-agarose gel product of Procedure A with the Cohn III extract of paragraph B 1) containing 2,000-4,000 CTA units of plasminogen at 4° C. for 5 hours.

3. Pour the above mixture to a 2-liter sintered glass funnel equipped with suction flask. Apply vacuum to filter the solution until the gel is dry. Wash the gel with phosphate buffered saline, mixing with a stirrer for a few minutes. Then, apply the vacuum to filter the solution. Repeat the same process until the filtrate reads less than 0.05 at an optical density of 280 nanometers (O.D. 280).

4. Wash the gel with phosphate buffered saline containing 0.1 M lysine at pH 7.4. Add 100 ml. of this solution to the gel and mix well before applying vacuum. Collect the filtrate. The washing procedure is repeated until the filtrate reads less than 0.05 at O.D. 280. Combine these filtrates and designate it as the lysine eluate. It contains highly purified plasminogen.

5. Add solid ammonium sulfate to the lysine eluate (400 g/liter), mix well, and store at 4° C. for 3 hours. Then, centrifuge at 12,000xg for 30 minutes. The precipitate is taken up in small quantity of phosphate buffered saline.

6. Dialyze the concentrated plasminogen against phosphate buffered saline (2 liters) for 24 hours with at least three changes of buffer.

7. Sterile filter the concentrated plasminogen through a 0.22-micron porosity membrane and store it aseptically.

C. Preparation of Sterile Human Plasmin

1. Add, aseptically, an amount of autoclaved 50% aqueous glycerol to an equal amount of the sterile plasminogen concentrate and keep it aseptically at 35° C. for spontaneous activation.

2. Withdraw samples aseptically from the plasminogen — 50% glycerol solution and during the period of activation assay for plasmin and plasminogen by the Hammarsten casein method.

3. When the activation is complete, which usually takes from one to two weeks, the concentrated plasmin is adjusted to pH 3.6 by addition of 0.1 M HCl and pasteurized at 60° C. for 10 hours. Then, the solution is readjusted to pH 7.4 by addition of 0.1 M NaOH.

D. Reaction of Plasmin with Immune Serum Globulin Solution

1. Add sterile plasmin to sterile immune serum globulin (16.5% protein, 0.2% NaCl, 2.25% glycine at pH 6.8) at a ratio of 0.5 to 1.0 CTA unit to 1 ml. solution and incubate at 21° C. (room temperature) for 2 to 9 days. Protein distribution profile by dextran gel (Sephadex G-200, Pharmacia AB) column chromatography and anticomplementary activity are determined.

1. When the anticomplementary activity is reduced to a level of about 10 mg./ml./2CH5O or higher, the reaction is stopped by addition of bentonite (25 mg./ml.), mixing thoroughly with the solution for 1 to 2 hours. Bentonite is removed by centrifugation at 12,000 g. for 20 minutes. The supernatant solution is then sterile filtered through a series of membranes of decreasing porosity to a mean pore size of 0.22 to 0.3 microns. In typical reactions using the procedure of paragraph (D 1), and using a ratio of 0.5 CTA unit of plasmin to 1 ml. of normal immune serum globulin and an incubuation time of two days, the anticomplementary activity of the modified globulin was lowered to 23 mg./ml./2CH5O. Similarly, under these same conditions except that the normal ISG was replaced by Rho(D) immune serum globulin, the anticomplementary activity of the modified Rho(D) globulin product was lowered to 2.2 mg./ml./2CH5O. By increasing the incubation time and plasmin concentration the anticomplementary activity is reduced even further. For example, in typical runs, the anticomplementary activity of normal immune serum globulin and Rho(D) serum globulin, using a nine day incubation and 1.0 CTA unit of plasmin to 1 ml. of globulin solution, is reduced to 50 mg./ml./2CH5O and 26 mg./ml./2CH5O, respectively.

HAMMARSTEIN CASEIN ASSAY FOR PLASMINOGEN

CASEIN PREPARATION

1. Dissolve 20 grams of Hammarstein Casein in 600 ml. of water by first adding small amounts of water and stirring sufficiently to make a thick paste. After all the water has been added, complete solution is effected by adding 0.2 N NaOH with stirring (not to exceed pH 8.0 at any time) and heating in a boiling water bath for 10-15 minutes to complete solution.

2. Cool to 2°-4° C. and quickly add with stirring 20 ml. of 1 N HCl. Continue addition until the pH is approximately 2.0. If any precipitate occurs, stir until it dissolves.

3. Add 200 ml. 7% trichloroacetic acid with stirring.

4. Centrifuge for 20 minutes at 2000 r.p.m. and decant away the supernate.

5. Wash once with 200 ml. of water by pouring the water on the precipitate in the centrifuge bottle and stirring to a suspension with a rubber policeman.

6. Centrifuge again at 2000 r.p.m. for 20 minutes and decant away the supernate.

7. Suspend the final precipitate in 150 ml. of 0.1 M phosphate buffer (pH 7.4) by stirring with a magnetic stirrer.

8. Dialyze against 0.1 M phosphate buffer until all the casein is in solution and the pH is 7.4 plus or minus 0.2. Twenty-four hours and two changes of buffer are usually sufficient. The optical density should be between 60 and 70 units/ml.

9. Store at −20° C.

PROCEDURE

Pipette 0.1 ml. of 1.0 M phosphate buffer (pH 7.4), up to 0.8 ml. of the plasminogen test solution, 0.1 ml. urokinase solution (2,500 Ploug units/ml.) and enough water to make a total of 1 ml. into a test tube. A blank of the same volume should be made using the same reagents, excluding the plasminogen solution. Pre-incubate these solutions for 10 minutes in 37° C. water bath. Add 1 ml. casein solution to each tube and incubate at 37° C. for 1 hour. Stop the reaction after exactly 1 hour by pipetting in 5 ml. 7% trichloroacetic acid. Masticate the precipitate with a stirring rod and post-incubate for 30 minutes at 37° C. Centrifuge at 2000 r.p.m. for 10 minutes. Decant off the supernate through a glass wool plug. Read the supernate optical density at 280 nanometers on a spectrophotometer, using 7% trichloroacetic acid as the standard. A standard curve can be made by using standard plasmin solution (American Red Cross) at various concentrations (between 0.1 CTA unit to 1.5 CTA units). The activity of the unknown solution can be determined from the standard curve.

While the invention in a process for producing immune globulin has been described in detail, it will be realized by those skilled in the art that considerable variation can be made in such detail without departing from the spirit of the invention as claimed below. It is intended therefore that the claims which follow should be interpreted to cover the invention and any such variation.

We claim:

1. Process for producing immune globulin for intravenous administration which comprises
    adsorbing plasminogen deriving from blood of a selected mammalian species on an adsorbent substrate of L-lysine agarose,
    washing the adsorbate to elute impurities,
    eluting the purified plasminogen from the substrate,
    converting the eluted plasminogen to plasmin,
    incubating a mixture of said plasmin and a quantity of homospecific immune globulin having anticomplementary activity under conditions such that the anticomplementary activity is substantially reduced,
    inactivating plasmin present in said mixture by adsorption on an inactivation adsorbent for plasmin, and recovering the immune globulin.

2. Process according to claim 1 wherein the L-lysine agarose substrate is an autoclavable L-lysine cross-linked agarose.

3. Process according to claim 1 wherein the eluted plasminogen prior to conversion to plasmin is purified by salting out, centrifugation and dialysis.

4. Process according to claim 1 wherein the plasminogen is converted to plasmin by means of activation with aqueous glycerol solution.

5. Process according to claim 1 wherein the incubation is carried out using 0.5 to 1.0 unit of plasmin to each milliliter of immune globulin.

6. Process according to claim 1 wherein the incubation is carried out for a period of from 2 to 9 days.

7. Process according to claim 1 wherein the incubation is carried out until the anticomplementary activity of the modified immune globulin is at a level of at least about 10 mg./ml.2CH5O.

8. Process according to claim 1 wherein the incubation is carried out such that fragmentation of the immune globulin is not more than 25%.

9. Process according to claim 1 wherein the inactivation adsorbent for plasmin is bentonite.

10. Process according to claim 1 wherein the L-lysine agarose substrate comprises an L-lysine epichlorohydrin cross-linked agarose.

* * * * *